United States Patent
Thorner

(12) 
(10) Patent No.: US 6,238,411 B1
(45) Date of Patent: May 29, 2001

(54) INTERNAL NASAL DILATOR

(76) Inventor: Robert H. Thorner, P.O. Box 82021, Rochester Hills, MI (US) 48308

( * ) Notice: Subject to any disclaimer, the term of this patent is extended or adjusted under 35 U.S.C. 154(b) by 0 days.

(21) Appl. No.: 09/204,677

(22) Filed: Dec. 3, 1998

Related U.S. Application Data

(60) Provisional application No. 60/069,765, filed on Dec. 16, 1997.

(51) Int. Cl.$^7$ .................................................. A61M 29/00
(52) U.S. Cl. ............................................................. 606/199
(58) Field of Search ........................... 606/204.45, 199; D24/141; 128/207.13, 207.18, 203.22

(56) References Cited

U.S. PATENT DOCUMENTS

| | | | |
|---|---|---|---|
| 576,441 | * | 2/1897 | Farmer .................................. 606/199 |
| 1,014,076 | * | 1/1912 | McConnell ........................... 606/199 |
| 1,069,459 | * | 8/1913 | Myles .................................... 606/199 |
| 1,077,574 | * | 11/1913 | Woodward ............................ 606/199 |
| 1,743,993 | * | 11/1930 | Washington .......................... 606/199 |
| 2,010,485 | * | 8/1935 | Heath .................................... 606/199 |
| 4,201,217 | * | 5/1980 | Slater .................................... 606/199 |
| 5,931,854 | * | 8/1999 | Dillon .............................. 606/204.45 |
| 6,093,169 | * | 7/2000 | Cardoso ................................. 604/94 |

* cited by examiner

Primary Examiner—Henry J. Recla
Assistant Examiner—(Jackie)Tan-Uyen T. Ho

(57) ABSTRACT

The anti-snoring invention comprises as internal nasal dilator having a combination of elements constructed and arranged to provide near-normal breathing for the wearer, while preventing the dilator from falling out of the nose, and without annoyance or discomfort for the wearer. To carry out the inventive concept, the internal dilator comprises a combination of several elements. First a V-shaped member, such as a flat spring is provided, with resilient pad means attached at each end thereof. A flexible nasal strip is then attached by the wearer at the central portion (outside bottom) of the V-shaped spring by adhesive means in one form of the invention, or by clamping means in another form; the nasal strip has two adhesive portions at or near the free unattached strip-ends. The spring-ends with the pad means are inserted by the wearer inside the two nostrils so the spring can spread the outer walls of the nose to increase the nasal opening for improved breathing. The adhesive portions at the free strip-ends are then pressed against the outer surfaces of the nose by the wearer to be attached thereto, for retaining the pad means in place inside the nose, so the spring and pad means do not fall out; the soft resilient pad means then prevent discomfort for the wearer. The used nasal strips are replaced daily for good hygiene, and the two pads are replaced once every 20-30 days.

38 Claims, 2 Drawing Sheets

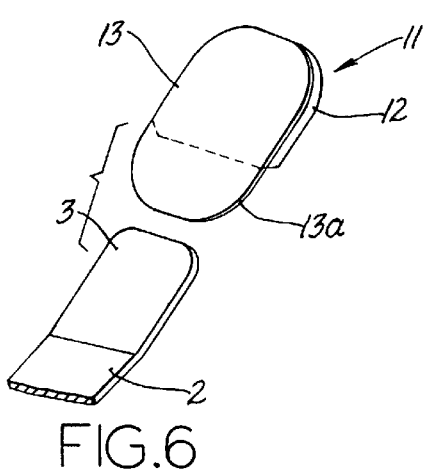
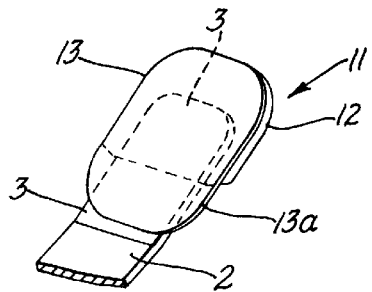
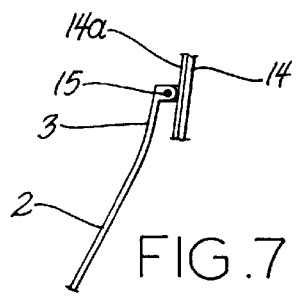
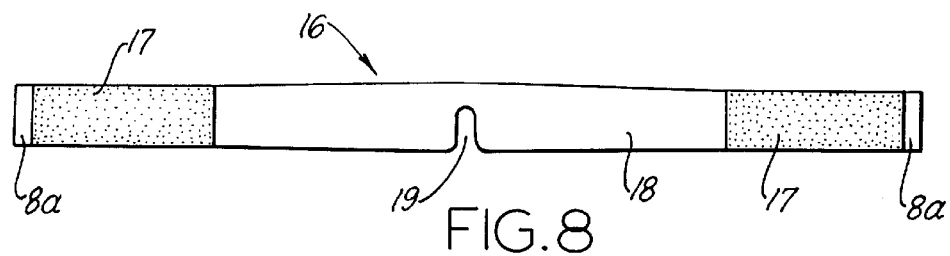
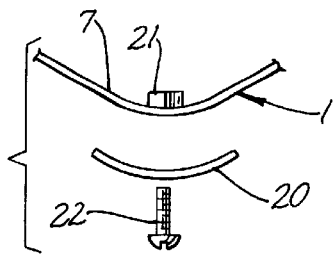
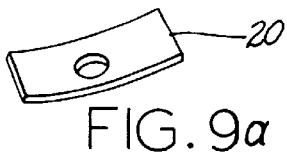
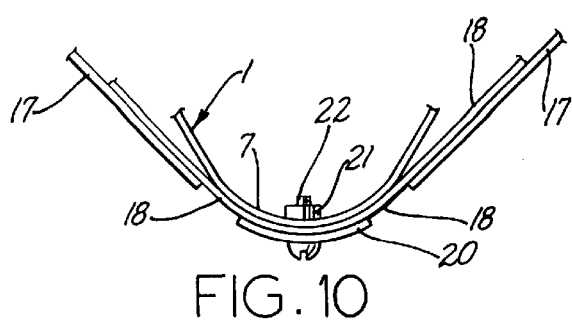

INTERNAL NASAL DILATOR

This Application claims the benefit of Provisional No. 60/069,765 filed Dec. 16, 1997.

BACKGROUND OF THE INVENTION

The present invention relates to an internal dilator (nose spreader) to expand the nasal passage (opening) in the nose of the user for producing substantially normal air-flow therethrough to reduce or eliminate snoring. The nasal dilator of the present invention overcomes the inherent detrimental problems and limitations of all known dilators, both internal and external.

The present invention is an outgrowth of my 24-year study of sleep as a research engineer. This long study resulted in my invention and development of a new sleeping system (bed) producing a deep sleep that greatly improves the quality of sleep while reducing the required time for the deep sleep to about 4½–5½ hours nightly from a normal of 7–8 hours.

It was clear in this long research that snoring severely detracts from the quality of sleep, and can cause several serious problems. Highway experts, engineers, medical people and state police everywhere all confirm that sleep deprivation is the cause of a large number of serious auto accidents with thousands of deaths and injuries, second only to drunk driving. From my sleep studies, I believe sleep deprivation is equal to or greater than drunk driving as a factor in auto accidents; I am convinced that 90–95% of all people have some degree of sleep deprivation as a result of poor beds, snoring and apnea. A recent Harvard study concluded that snoring and apnea increase the chance for an auto accident seven times.

Automobile engines provide an excellent analogy for the problems of sleep. The total horsepower (HP) produced by fuel and air entering an auto engine is called "indicated HP". Then the power just to run an inactive engine (as by an electric motor) is called "friction HP". The "brake HP" is the difference between the indicated HP and friction HP, and is the power available to run an automobile in travel, up and down hills, etc. A low friction HP provides more brake HP available for driving a car.

Similarly, the human "engine" requires fuel (food) and air plus the mysterious ingredient of sleep, to produce a total energy (comparable to indicated HP). When we sleep, our bodies slow down and the energy required to operate our "engine" in deep rest is reduced and can be compared to the friction HP of an auto engine.

Then the energy we have to use the next day is the difference between the total energy produced by our fuel (food) and air and the energy required when sleeping; and this difference can be compared to the brake HP of an engine. Deeper sleep requires less energy, so more energy is available the next day for our life activities. Any noise made by the sleeper, such as snoring, needs much energy which is wasted, so the sleeper has less energy to "spend" the next day.

In other words, sleep builds up an "energy bank" to be used the next day (like brake HP). Snoring requires a lot of energy, as do bells, horns, or any noise-maker. Hence when people snore, some of the "energy bank" is wasted in producing the noise, so less energy is available the next day thereby producing sleep deprivation. In view of all the foregoing, it is indeed worth the effort to eliminate or reduce snoring.

In order to appreciate the great utility of the present invention, it is first necessary to consider the problems of snoring, and particularly why past dilators have failed to overcome these problems.

Doctors tell us that we should breathe only through our nasal passage because the air is warmed, moisturized, and filtered. Unfiltered air that reaches the lungs by mouth-breathing can cause lung problems because of contaminents carried by the air.

Snoring is produced when the nasal passage is abnormally restricted to cause mouth-breathing, especially when the sleeper rests on the back. The total nasal "passage" actually includes two openings formed by the septum. Hence any abnormal restriction of air-flow through the nasal passage can cause mouth-breathing and subsequent snoring by vibration of the tissues in the tongue, uvula and/or throat. This condition in extreme can also cause apnea, in which the sleeper gasps for air suddenly and often stops breathing because of oxygen deficiency, which can cause a heart attack and even death.

It is a principle of fluid dynamics that if an air passage includes a plurality of possible restrictions and one restriction is removed, the air passage can still be blocked if any one of the other possible restrictions fully or partly blocks the passage.

There are four possible factors that can cause a restriction of air through the nasal passage; (1) An abnormal restriction of the openings in the "nasal-valve" area. The nasal valve is a slight but normal narrowing of the nasal openings near the entrance of the nose; (2) Sinus problems can also cause an abnormal restriction of the nasal passage, (3) The turbinates, located in the inner surface of the outer wall of each nostril, can expand to cause an abnormal restriction of the nasal openings (to be discussed); (4) a deviated septum can also cause a restriction of the nasal openings; and (5) polyps develop, which can easily be removed by doctors.

Any one or more of these five factors can cause sufficient restriction of the nasal passage to produce mouth-breathing. Then the air-flow past the tongue surface and uvula can cause the tissues thereof to vibrate and produce snoring. Hence, any one or more of these five factors can indirectly cause snoring by forcing the sleeper to breathe through the mouth.

While a restriction in the nasal-valve area is probably the most common of the factors causing snoring, I am convinced that 90% of people who snore have more than one problem causing their snoring; they must identify their particular problem(s) with the help of an ENT doctor (ear, nose and throat), and when treated, there is a good chance they can end or reduce their snoring.

All nasal dilators, including the dilator of the present invention, can help only a restriction in the nasal-valve area, which might be the only problem. However, if a sleeper has a snoring problem in the nasal-valve area plus a sinus problem and/or a turbinate problem, for example, the new nasal dilator plus the help of an ENT doctor may enable the sleeper finally to overcome the snoring problem.

More specifically, the nose filters, warms, and moistens the air before entering the lungs. The nose contains a septum (the wall between the two nostrils) comprising cartilage and bone covered by a layer of mucous membrane. The sticky mucous lining of the nose and nasal passages provides a filter action, trapping dirt particles and bacteria in the air with the help of small hairs that project from the cavities.

Three turbinates are located on each of the insides of the outer walls of the nasal passage, separate from the septum. The turbinates are thin curlicues of bone with thick membranes curving from the outer part of the nose toward the septum. Erectile tissue is under the mucous membranes and is sensitive to temperature, causing tissues of the area to swell with the influx of blood when the air is dry, cold and/or contaminated with pollen, humidity, dust, allergens, etc. The turbinates warm and moisten the air in normal breathing. When the turbinates become erect, they swell to narrow the passages and produce mucus which causes the nose to run, especially when the sleeper is cold. If the nasal passages are abnormally narrowed by turbinate swelling, normal air-breathing is restricted enough to cause mouth-breathing and snoring. ENT doctors can treat this condition by relatively simple procedures with a high degree of success.

A sinus problem can restrict the nasal passages, and can be treated successfully by ENT doctors, especially with a relatively new minor operation. A deviated septum that restricts the nasal passage can also be corrected by an operation with a high degree of success.

I was motivated to develop the dilator of the present invention because my snoring detracts from the improved sleep produced by my new sleeping system. Because of the inherent restriction in my nasal valve area my breathing is about 60% of normal. I tried both internal and external dilators now on the market. One external dilator improved my breathing from 60% of normal to only about 70%, and the strong adhesive force irratated my skin which became red after only a few days of use; these characteristics are inherent in all external dilators, to be discussed.

The dilator of the present invention improved my breathing to at least 90% of normal and has not irritated my skin after about three years of use, all for reasons to be discussed. Also, the new dilator is not annoying and does not fall out. By contrast, internal dilators now on the market are annoying and/or fall out, which was my experience when using these nasal dilators.

The several causes of snoring because of mouth-breathing are important, but secondary since we are not supposed to breathe through our mouths. Hence, the first and major effort should be to do whatever is necessary to produce nasal breathing with the mouth closed, so air cannot flow through the mouth to produce snoring.

However, it is possible for some people to have an open nasal-passage and still breathe through the mouth if the lips are open. For proof, when a sleeper breathes through even a slightly open mouth, and then closes the lips while breathing out, nasal breathing is instantly restored. With this mouth-breathing, opening the nasal passage would do no good. This condition can occur because if both the nasal and oral passages are open, mouth-breathing is the path of least resistance for air-flow. For some people this condition might be overcome by keeping the head from tilting back by using a special pillow, or as explained in the next paragraph.

For snorers who breathe through the mouth even though the nasal passage is open and cannot correct this condition, then as a last resort, a direct solution for mouth-breathing is better than nothing—at least the noise and energy-loss are often eliminated. These "solutions" include fixtures by dentists to prevent the tongue-surface from vibrating; or surgical removal of tissues in this area, as by a recent improved procedure using radio frequency. Sometimes removal of all or part of the uvula helps but not always. However with these last-resort "solutions", the sleeper still breathes through the mouth, whereas proper breathing should be done through the nasal passages, according to doctors.

Snorers first must be patient in trying to solve any or all problems in the nasal passage. But a solution for the restriction in the nasal valve area is essential since doctors have no solution for this problem; only a good nasal dilator, when available on the market, can help to overcome this problem.

In view of all the foregoing, this widespread and very serious problem of snoring can prevent sound sleep which also cause severe head-on auto accidents; so it is important to solve this problem. A restriction in the nasal valve area is the only factor causing snoring for a large share of snorers; but a solution for this problem can have no effect on a sinus problem, turbinate problem, or a deviated septum. However, people who have any of these other three problems often can be treated by an ENT doctor with a high degree of success, as discussed.

SUMMARY OF THE INVENTION

The nose-spreader (dilator) of the present invention enables the user to breathe better. The dilator illustrated herein comprises a thin U or V-shaped member, preferably a spring (hereinafter referred to as UV-spring); the preferred forms of the invention include thin pads at each spring-end for soft contact on the nasal surfaces when the two spring-ends are inserted, each in one of the two nostrils to expand the nasal opening.

The UV-spring is retained in the nose by a flexible nasal strip with an adhesive segment at its center for connection with the central portion of the spring and with adhesive segments at or near the extremities thereof. In another form of the invention, the nasal strip includes a flexible plastic strip with an aperture, such as a partial slot-opening at its center, to be clamped between a clamp-piece and the UV-spring; in this form of the invention, the clamp-piece and plastic strip are retained in one form of nasal strip, by a small screw and a nut secured to the UV-spring. In both forms of the invention, the plastic strip has adhesive segments at or near the free ends thereof that are pressed onto the sides of the nose by the user or wearer; but at the very ends of the nasal strip, small non-adhesive portions can be provided to enable easy peeling of the strip from the skin. A piece of adhesive alone with the non-adhesive portions at the ends can be used, but the two forms of nasal strips shown herein are preferable.

In all forms of the present invention, the spring force is independent of the adhesive (stick) force; therefore, both the adhesive force and area of skin contact can be small because the adhesive segments only need to keep the UV-spring from falling out.

All past "external" nasal dilators shown in the patent art and on the market, comprise nasal strips which include adhesive segments at the extremities thereof to stick on the outer nasal skin. These dilators also include spring means as part of each nasal strip for pulling on the outer nasal surface to open the nostrils. Therefore, all external dilators must provide a spring-force that inherently is less than the stick-force of the adhesive. If the spring-force were larger than the stick-force, the dilator would not stick to the nose. This inherent limitation of all external dilators explains why they can produce only a very slight improvement in breathing, at best. By contrast, because in the present invention the spring-force is independent of the stick-force, the adhesive-area on the skin and the stick-force can inherently be much smaller than for all external dilators, since the adhesive only must keep the dilator from falling out, as discussed. Also, the spring-force of the instant invention is adjustable (selective) for any degree of nose-spreading.

Hence, with all external dilators, the adhesive force and the adhesive area inherently must be very large (agressive)

to overpower the light spring-force at all times. Because of the light spring force, a relatively small increase in breathing is produced. Since the UV-spring of the present invention is independent of the stick-force, the new dilator can produce a much larger nasal opening because of the variable (selectable and larger spread-force. In fact, the adhesive area of the nasal strip of my dilator is less than one-half of the area of skin-contact and with a much lower "peel" force than for external dilators.

The stick-force of all external dilators must inherently be so strong that the skin is pulled unpleasantly hard upon removal of the dilator (feels as though the skin is being pulled off). Worse, the essential large stick-force might cause serious problems on sensitive skin after 8–10 years or more of daily use.

OBJECTS OF THE INVENTION

A main object of the present invention is to provide an internal nasal dilator with a U or V-shaped member, preferably a spring, constructed and arranged to spread the nasal walls for increasing air-flow through the nasal passage to enable normal breathing, whereas all external dilators inherently produce limited opening of the nasal passage;

Another object of the present invention is to provide an internal nasal dilator as set forth in the prior object that includes a nasal strip attachable to the UV-spring at the central portion thereof and having adhesive segments at or near the ends adapted to be pressed onto the outer surfaces of the nose to hold the spring in place; and further in which the adhesive-force and area required is much less than the adhesive-force and area inherently required for all external dilators, so the adhesive can be easily removed with a light force that does not irritate the skin, as do past external dilators;

An additional object of the present invention is to provide an internal nasal dilator as set forth in the preceding objects that can easily be installed and removed in a few seconds;

An important object of the present invention is to provide an internal nasal dilator as set forth in the preceding objects that includes a nasal strip which inherently can be manufactured and sold at lower cost than all external dilators, and which requires that the spring for spreading the nasal walls is a part of every nasal strip sold to the public, whereas the spring of the dilator of the present invention inherently is separate from the nasal strip to be sold (only once) to customers;

A further object of the present invention is to provide an internal dilator as set forth in the prior objects that enables selective adjustment of the spring-force to any desired amount to produce almost normal opening of the nasal valve area whereas the spring-forces of all external dilators are inherently limited to be less than the adhesive force of the nasal strip, and are not adjustable thereby producing a limited nasal opening far less than normal;

Another object of the present invention is to provide an internal dilator as set forth in the prior objects which does not fall out of the nasal passage because the adhesive segments of the nasal strip are pressed onto the outer surfaces of the nose to retain the dilator in place; and the dilator does not annoy the user, whereas past internal dilators tend to fall out and/or annoy the user.

Other objects and advantages of the invention will become apparent from the following description, and from the accompanying drawings, in which:

FIG. 6 is a perspective enlarged view of another form of a separate pad that can be used for the single contact on the skin inside each nostril;

FIG. 6a is another view of the pad illustrated in FIG. 6 as installed on the spring extremities;

FIG. 7 is an elevational side view of still another form of pad for contacting the inner nasal wall and intended to provide self-alignment contact and hence lower pressures on the inner nasal walls;

FIG. 8 is an elevational view of another form of the nasal strip that can be used to retain the UV-spring of the internal dilator;

FIG. 9 is an elevational exploded side view of the parts required to clamp the nasal strip shown in FIG. 8 to the spring; FIG. 9a shows the clamp;

and FIG. 10 is an elevational side view of the assembly of the nasal strip and parts shown in FIGS. 8 and 9 when attached to the UV-spring.

It is to be understood that the invention is not limited in its application to the details of construction and arrangement of parts illustrated in the accompanying drawings, since the invention is capable of other embodiments and of being practiced or carried out in various ways. Also it is to be understood that the phraseology and terminology employed herein are for purposes of description and not of limitation.

DESCRIPTION OF THE INVENTION

The following is a discussion of the various forms of the invention illustrated herein to show how the dilator when made according to the present invention provides the benefits set forth in the objects.

Figure 1:
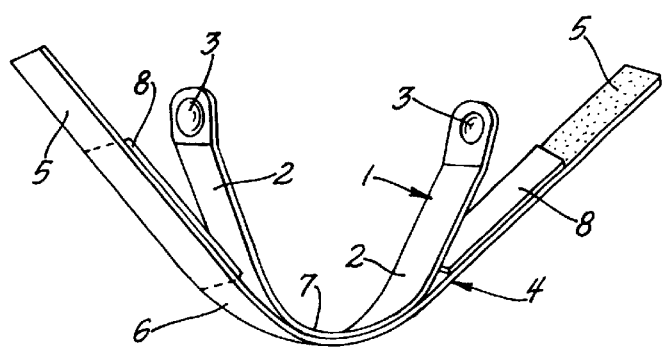
FIG. 1 is a perspective view of the internal dilator showing the UV-spring with one form of nasal strip attached thereto.
Figure 2:
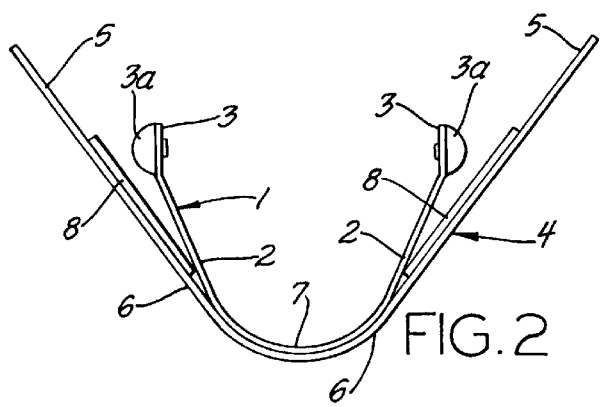
FIG. 2 is an elevational side view of the internal dilator of FIG. 1, showing rounded pads at the extremities of the UV-spring.

In FIGS. 1 and 2 by way of illustration, the dilator of the present invention includes spreading means comprising a thin U or V-shaped spring 1 preferably made of thin flat spring material (hereinafter referred to as a UV-spring, or just "spring") having leg-portion 2 with contact-portions (or tab portions) 3 or 3a at the ends of the spring and adapted to be inserted inside the nostrils of the user free of contact with the septum to increase the nasal-openings. The UV-spring is shown with its ends apart in the free position. The contact-portions 3 in the simplest form can comprise merely rounded concave-shaped ends of the spring with a soft plastic coating, or preferably by separate thin rounded pads made of resilient material, for example, attached to contact-portions 3. The contact-portions 3 and 3a are smooth and rounded to minimize the awareness of the dilator by the user.

In FIG. 2, the contact-portions are shown as separate rounded pads 3a, such as soft plastic or other resilient material secured to the contact portions 3. If the pads are made of spherical shape, they would provide the same contact-shape regardless of the angle of contact-portion 3.

Any nasal dilator, both internal and external, will cause the user to be aware of its presence, and requires one to three weeks for the user to be unaware of the device and resume normal sleep; hence, the user must be patient. If the edges of the contact portions were not rounded, the dilator would be annoying. There is a difference between awareness and annoyance; the user would always be aware of the dilator if it is annoying.

The UV-spring is preferably made of a very thin flat spring material such as phos-bronze or stainless steel treated for spring action, and about 0.008–0.010" thick. Since the UV-spring is so thin, it has rather sharp edges. Hence, the spring is preferably coated along its entire length (except for contact-portion 3) with about 0.010 inch of a soft rubber or plastic, like urethane or silicon for example, to round the edges; this is done for baby's spoons with a coating of about 0.010" to prevent the sharp edges of the spoon from cutting the baby's mouth.

A plastic UV-spring (or even spring wire) can be used; but actual tests of the dilator have shown that a flat metal spring material is preferable because it can more easily be bent to enable selective adjustment of the spring-force, and will maintain this force as long as the spring operates within its elastic limits. The UV-spring is retained in the nose by one form of nasal strip 4 shown in FIGS. 1–3. This nasal strip, shown best in FIG. 3 (stick-side up) comprises three thin adhesive segments (shown stipled) and two non-adhesive segments. The two end adhesive segments 5 are near the ends of the nasal strip, and are pressed against the skin by the user to retain the dilator so it does not fall out. The mid-adhesive segment 6 of the nasal strip is pressed against the central portion 7 of the UV-spring (at the bottom) by the user for connection therewith to retain the nasal-strip in proper position in relation to spring 1. The strip also includes narrow non-adhesive portions 8a at the ends (or only at the corners). For centering means, a centered hole or aperture 6a of nasal strip 4 is placed over a pimple (not shown), or other projection means, of the UV-spring disposed to enter into hole 6a at the center of strip 4, for example.

The non-adhesive segments 8 and 8a have several important functions in the use of the dilator. First, the non-adhesive segments 8 enable the user to install the dilator without the adhesive sticking to the fingers. Second, and very important, these non-adhesive segments determine where the end adhesive-segments 5 will be best applied to the skin, since a minimum amount of skin-contact is desired. These segments should be pressed against the skin mostly above the "flange 9a" and rubbed firmly to be sure the dilator is retained in place. The non-adhesive segments 8 of the nasal strip are sized so that the largest parts of the adhesive portions 5 cover the "hard" part of the nose, and a smaller part of each adhesive-portion 5 covers the flange of the nose. The non-adhesive portions 8a enable easy removal of the strip.

The non-adhesive segments 8 can be a lack of adhesive on strip 4, or a pair of thin semi-rigid but fairly flexible plastic pieces. The plastic strip gives some rigidity and shape to strip 4 when attached to spring 1 by adhesive segment 6; also, the length of the non-adhesive pieces 8 can determine that the end-adhesive segments 5 start near the top of the "flange" of the nose, so that much of the end adhesive-segments 5 will cover the hard part of the nose. It is desirable for the adhesive to cover the least amount of skin as possible; hence, the adhesive should be applied where it will do the most good—largely on the upper "hard" part of the nose where it can be pressed and rubbed firmly against the skin.

All portions and segments of the nasal strip comprise very thin material that would appear merely as lines in a true proportional drawing. However in order to illustrate the proper relative positions of elements of the nasal strips, they are shown with thickness in the drawings, although too thick for proper proportion. Actually, the spring is about 0.008–0.010 inch thick, the plastic pieces 8 are about 0.007–0.009 in. thick, and the adhesive material is about 0.005 in. thick.

To install the dilator of the present invention, the contact-portions 3 of the UV-spring 1 are inserted into the two nostrils so the lower ends of the contact-portions with pads 3a are just visible, or if more comfortable, install just above or near the nasal flange area. The forefinger is then used to slide one side of the nasal strip against one side of the nose, and then on the other side alternately; then the adhesive segments are pressed to adhere to the nose, and rubbed firmly. The adhesive segments 5 provide a strong shear force but are removed easily with a light force when sleep is over by peeling the adhesive-segments 5 outwardly from each side of the nose, starting from the top with the non-adhesive portion 8a. An adhesive (preferably translucent) with a light stick-force can be used for the adhesive segment, such for example, as 3M Medical Tapes Nos. 1505, 1515, 1529.

Figure 3:
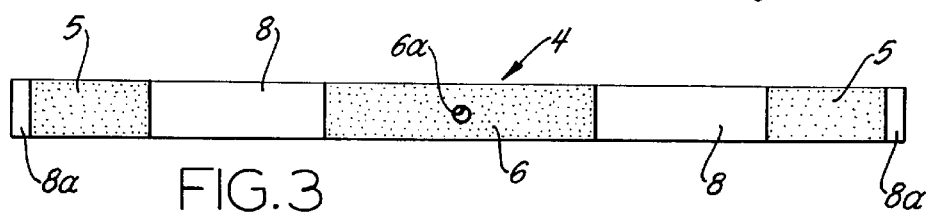
FIG. 3 is an elevational view of one form of nasal strip illustrated in FIG. 1, as it would be sold to the public.
Figure 4:
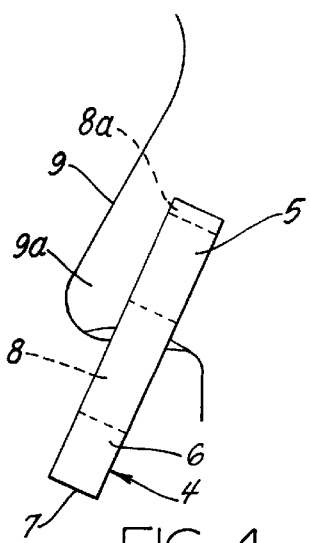
FIG. 4 is a side view of the nose with the internal dilator of FIGS. 1–3 attached thereto by adhesive segments of the nasal strip when installed by the user.
Figure 5:
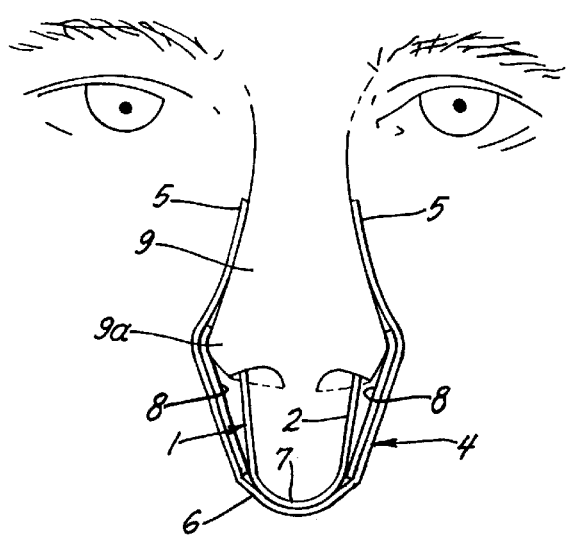
FIG. 5 is a front view of the internal dilator shown in FIG. 4 with the extremities of the spring inserted in the nostrils of the user and showing the nasal strip of FIGS. 1–3 with the adhesive segment attached to the nose.

The spring-force is adjusted to the amount that gives the best breathing and is not annoying. A ruler is used to measure the spread-distance between the free spring-ends. At first, the spring is adjusted by slight bending at the central-portion 7 to spread the nose slightly. The spread-distance is increased by 1/16 inch each time until breathing no longer increases. This distance, or slightly less, will give the maximum breathing for the user. FIGS. 4 and 5 show the dilator of FIGS. 1–3 (with corresponding numerals) installed in the nose 9. The adhesive-segments 5 of the nasal-strip 4 are positioned to start at about the top of the nasal "flange" 9a, as determined by the length of the plastic pieces 8; and the rest of the adhesive segments are pressed against the upper hard part of the nose.

FIG. 5 is a front view of the dilator installed as viewed in FIG. 4 showing corresponding numerals.

FIG. 6 shows another form of contact unit 11 which includes a covered pad 12 comprising a resilient material with rounded edges such as a soft urethane foam core enclosed by a cover formed by three pieces of thin flexible plastic film (about 0.003"–0.004" thick), the film pieces are heat-sealed together on all edges. The foam core is covered on all sides by two pieces of the thin plastic film. A third piece of thin plastic film 13 is heat-sealed at its extremities on three sides along with heat-sealing the cover for the foam pad to form a thin pocket between the plastic film 13 and the adjacent cover for the foam pad 12.

The plastic film 13 has an extension 13a which serves several purposes. First, it enables the contact-portion 3 of spring 1 to be guided snugly into the said pocket formed by the extension 13a as shown in FIG. 6a; the tolerances can be very tight so the ends of the contact-portions 3 are inserted into the pockets with a fairly large force (and requires a large force to remove) so the pads do not fall out.

A second use of extension 13a could be to provide an additional holding-force, by coating the inner side of the extension with a strong adhesive to be pressed onto the leg-portions 2; however, extensive use of the contact-unit 11 viewed in FIG. 6 has shown that a tight-fit is sufficient to prevent the pads from falling out. The contact unit 11 seems to work very well in actual use with minimum awareness for the user. Since the soft foam pads 12 take a permanent set after several months, the contact units 11 should be replaced every 15–30 days with the new units merely by pulling the pads off the contact portions 3, and the new units are forced onto contact-portions 3 which are inserted into the pocket formed by the film 13. The nasal strips should be replaced daily for good hygiene.

Another form of contact-portion 3a at the ends of spring 1 has been used, but is not shown herein. The pad is made of uncovered soft foam (like urethane foam) about 1/16" thick, for example, to provide a degree of self-alignment. The pad has rounded edges and an adhesive backing for attachment to the contact-portion 3. These pads with soft adhesive-backed foam take a permanent set after a few months, and are removed by scraping off with a knife to be replaced by new pads. The tab portions of contact-portions 3 of the UV-spring 1 are shown in FIGS. 1 and 2 as bent inward to help align the pads with the normal inner surface of the nostril-walls.

FIG. 7 is another form of contact-unit comprising a permanent pad 14 made of rubber-like material attached to a base 14a with a hinge 15 connected to the end of each leg-portion of the spring 1. This construction provides self-aligning contact of the pads against the inside walls of the nose to minimize awareness by the user, like self-aligning pads for eye-glasses that rest on the nose; but unit 11 is preferred.

All pads should be cleaned daily for good hygiene using the wearer's face soap or a mild anti-bacterial soap. The area of skin contacted by the adhesive should be washed with the user's face-soap and dried thoroughly before installing the dilator. The unit can be installed in 5–8 seconds.

FIG. 8 illustrates a second form of nasal strip 16. In this form of the invention, a single strip of thin adhesive-backed piece 17 of proper length (shown stick-side up) includes a non-adhesive segment 18 at the major section of the center of the strip 16. The small non-adhesive portions 8a are at the very ends as in FIG. 3. Preferably,the non-adhesive segment comprises a thin single semi-rigid but fairly flexible plastic piece 18 (0.007–0.009" thick) pressed onto the adhesive piece 17. The adhesive segments 17 can comprise a single piece or merely two pieces, each pressed on the plastic piece 18 (as shown in FIG. 10). The nasal strip 16 includes an aperture, such as a partial slot-opening 19 at its center for use now to be described.

FIG. 9 shows the means for connecting the nasal strip 16 to the central portion 7 of spring 1. A thin clamp-piece 20 preferably is made of spring metal and includes a hole at its center, as shown in perspective in FIG. 9a. The central portion 7 of spring 1 now includes a small nut 21 aligned with a hole in the spring and secured thereto, as by solder. A small screw 22 (with a 2-56 thread, for example) is adapted to be inserted through the hole in clamp-piece 20 and spring 1, to be retained by nut 21.

The entire assembly is illustrated in FIG. 10, and the parts are indicated by the proper numerals, all held together by the screw 22, clamp-piece 20, and nut 21. The nasal strip 16 is inserted between clamp-piece 20 and spring 1 at the slot 19 (see FIG. 8) after loosening screw 22 sufficiently to provide enough space. The strip is then carefully aligned with the spring 1, and the screw 22 is tightened so the clamp-piece 20 holds the nasal strip in place. A small screwdriver with A small handle to enable only finger-tightness can be provided. This assembly process can be done in only a few minutes.

The UV-spring 1 illustrated in FIGS. 1, 2, and 10 is shown wide apart in its free position, but can be set at any adjusted position to produce proper breathing. The pads may be inserted opposite the nasal flanges or slightly further up the nostrils near the top of the flanges of the nose, as desired to produce the least awareness.

Some views in the drawings are larger than actual size; and since the dilator is very small with thin elements, it is difficult to visulize the true structure of the dilator from the drawings. Hence, the present sizes of the dilator and components are as follows, although several sizes may be required: the spring 1 is about 2 7/8 in. long and 5/16 in. at its center and about 1/4 in. wide at the contact portion 3. The nasal strips of FIGS. 3 and 8 are about 4 1/4 to 4 3/4 in. long and 3/8" wide, and includes adhesive segments 5 and 17 which are about 3/4–7/8 in. long and about 3/8 in. wide. The plastic piece 18 is about 3/8 in. wide and 2 1/2–2 7/8 in. long. The UV-spring projects down from the nose about 3/4 in. when installed.

The present invention is intended to cover any kind of internal nasal dilator for causing the nasal passage to open and be retained by a nasal-strip including an adhesive segment adapted to be pressed onto the outer side of the nose. More specifically, my invention is intended to cover any kind of nasal dilator with a UV-member such as a spring having two leg-portions to be inserted in the nostrils without contacting the septum and retained by any kind of flexible member connected to the spring at its center which includes adhesive means to hold the dilator in place, all to cause the nostrils to open more for reducing snoring. However, the construction and arrangement of the combination of elements of my internal dilator with the specific forms of nasal strips, per se, as illustrated herein comprise particularly important concepts in the practice of the invention.

There are other possible arrangements of the elements of my dilator invention that produce the same operation and results as with the forms of the invention illustrated herein—but all such other arrangements are within the scope of my inventive concepts.

In the patent courts and Rules of Practice, in order for a patent to be valid, a true invention must be new and useful to a much higher degree than for mere design. The most certain proof of real invention over mere design is when it can be shown that the alleged invention has great utility over all previous efforts by many past inventors, as disclosed in all prior patents and other publications.

The best possible circumstances that prove such dramatic novelty and utility, and hence true invention, is when there is a serious and difficult problem of long-standing with many years of prior effort to solve this difficult problem by a large number of skilled workers in the field of the invention with limited or no success. These circumstances prove in fact how elusive a real solution for the difficult problem had been. Even if the real solution to this difficult problem turns out to be very simple, true invention indeed can be present if these conditions prevail. These are the exact circumstances that prevail to a high degree for the present invention, so the dilator disclosed herein meets all the requirments to comprise true invention, as will now be shown.

People have been snoring all over the world since the beginning of human existence. Hence as expected, there are an enormous number of patents by inventors who tried over many years to solve this difficult problem with little or no success. The novelty and utility of the present invention has been described above.

In professional patent searches relating to the present invention, pertinent patents were found going back over 100 years. These patents are of interest because they typify the enormous effort by a large number of inventors trying to provide a real solution to the problem of restriction in the nasal valve area for many years with little or no success—all proving how elusive a real solution for this problem has been. Some of these patents are as follows:

| Dayton | 513,458 | Jan. 23, 1894 |
|---|---|---|
| Farmer | 576,441 | Feb. 2, 1897 |
| Woodward | 1,077,574 | Nov. 4, 1913 |
| McConnell | 1,014,076 | Jan. 9, 1912 |
| Myles | 1,069,459 | Aug. 5, 1913 |
| Washington | 1,743,993 | Nov. 26, 1928 |
| Heath | 2,010,485 | Aug. 6, 1935 |
| Slater | 4,201,217 | May 6, 1980 |
| Johnson | 5,476,091 | Dec. 19, 1995 |
| Johnson | 5,549,103 | Aug. 27, 1996 |
| Munchin | 5,553,605 | Sept. 10, 1996 |
| Pertruson | 5,479,944 | Jan. 2, 1996 |
| Pertruson | Re.35,408 | Dec. 24, 1996 |

While none of these patents disclose the present invention, they do provide dramatic evidence of the enormous past efforts relating to nasal dilators, both internal and external.

Any internal dilator having a U-shaped spring should provide minimum awareness for the user. Hence, it is desirable to provide nasal pads at the spring-ends of relatively soft material with a smooth surface and rounded edges without projections and somewhat self-aligning, all as disclosed herein.

The spring-force needed to spread the nasal walls enough for normal breathing would not be sufficient to prevent the spring from falling out for 6–8 hours while the sleeper turns 30–50 times each night. Therefore the spring alone, especially if it includes the required smooth pads at the spring-ends, cannot keep an internal nasal dilator from falling out of the nose. If the spring-force were great enough to retain the dilator in place, it would be inoperative for practical use because it would be too annoying for the user.

In fact, any internal nasal dilator without a positive retaining means, as disclosed herein, will fall out of the nose in practical use, according to extensive evaluation of the dilator of the present invention; in this event, the dilator would be inoperative, or at least not useful for the purpose intended. Accordingly, any claim in a patent disclosing an internal dilator that does not include a positive and non-annoying retaining means recites an inoperative structure, so that any claim reciting this structure is invalid. An inoperative device is hardly "useful" beyond mere design, as required for patentability. However, patents disclosing inoperative structures can be considered as valid prior art for "equivalency" considerations; so that any combination of elements in a patent equivalent to an inoperative structure in prior patents is also inoperative, because the combination is not useful as required. This is all true even if the invention is operative but not useful beyond design.

Referring to the above patents for proof of a long effort by prior inventors, the Farmer and Dayton patents are over 100 years old. The Woodward, McConnell and Myles patents are almost 85 years old. The Heath and Washington patents are 60 and 70 years old, respectively—all disclosing internal dilators.

The two Johnson patents disclose an external dilator, and are of interest because they also show large activity for many years, since 20 patents were cited going back to 1910. similarly, in the Munchin patent for an external dilator, patents are cited back to 1902; in addition, 71 patents are listed as references.

The important definitive Farmer and Washington patents disclose internal dilators with U-shaped springs and soft pads for insertion in the nostrils, but these patents do not disclose a structure including a workable positive retaining means of any kind. The Farmer patent does disclose a soft rubber vacuum-cup intended to act as a retaining means, but in practice the cup would not hold vacuum for 6–8 hours; and worse, there is no way to press the cup down on a smooth hard surface to evacuate the air as required for any vacuum-cup. Without a workable retaining means, these internal dilators will fall out of the nose in practical use, so the disclosed devices are inoperative (or at least not useful) for the purpose intended.

The Woodward, Dayton, Myles and McConnell patents disclose internal dilators that include somewhat positive retaining means comprising various mechanisms to clamp the dilator to the bottom of the septum. However, my research has shown that the septum is very sensitive, so that such clamping means are annoying and are not useful, which explains why these devices have not found public acceptance in all these years.

The patents to Pertruson show an internal dilator, and are of interest mainly because 40 patents going back to 1902 are cited. In these patents in FIGS. 1–3, a spring having pads with smooth surfaces on the spring ends is shown, but no positive and workable retaining means are disclosed; hence these patents include structures that are "equivalent" to the inoperative structures in the Farmer and Washington patents (erroneously not cited in the Pertruson patents).

Also, the use of unworkable vacuum-cups is mentioned in the Pertruson patents, as in the Washington patent with similar failings. In FIGS. 5 and 6 of these patents, a plastic spring is shown with pads having a plurality of "protuberences" to comprise "gripping means" to keep the dilator from falling out; also, the "gripping means" includes unworkable suction cups. If these "protuberences" are intended to be equivalent to a positive retaining means, the structure has proven to be very annoying for practical use, and hence is not useful in actual practice. No positive and workable retaining means is shown in these patents. The largest complaint of all internal dilators in the past, as well as those now on the market, is that they are annoying and/or fall out.

In all the 100-year effort discussed above, it is now clear that many inventors tried to find a practical and workable solution for the problem of restriction in the nasal valve area with limited or no success. Inventors must disclose a real and complete solution for this long-standing problem in order to comprise real invention over mere design, even if the dramatic solution is very simple with only slight changes over the prior art.

For reasons explained above and confirmed by extensive medical tests, there is no doubt that any internal dilator inherently can expand the nasal passages dramatically more than any external dilator to provide near normal breathing for the user. According to snorers in a market-study, almost all of the people in the study have used external dilators now on the market, and they all advised that these dilators provide only a slight improvement in breathing (because of the inherent limitation explained above). The internal nasal dilator shown and described herein comprises for the first time a practical and very useful invention for providing a large enough opening of the passages in the nasal valve area to enable substantially normal breathing for the user.

When a solution to a difficult problem is beautifully simple, as disclosed herein, it often appears that nothing has been accomplished. Hence, it is hard to appreciate the value of a simple contribution unless the problem is clearly understood, as discussed above. Simple solutions to difficult problems are notoriously elusive—but it is easy for others with the real solution before them to consider the novel solution as obvious, with knowledge after the event. Under these circumstances when the particular combination of elements with a definite arrangement is startlingly simple, even if individual elements are found in other prior patents, the very simplicity is the height of invention. Most inventions comprise a new combination of all or mostly all old elements.

The question of invention is often controlled by the frequently cited holding of the Supreme Court in *Diamond Rubber Co.* v. *Consolidated Rubber Tire Co.,* 220 U.S. 428, in which the court said:

"Many things, and the patent law abounds in illustrations, seem obvious after they have been done, and, in the light of the accomplished result, it is often a matter of wonder how they so long eluded the search of the discoverer and set at defiance the speculations of inventive genius . . . Knowledge after the event is always easy, and problems once solved present no difficulties, indeed, may be represented as never having had any, and expert witnesses may be brought forward to show that the new thing which seemed to have eluded the search of the world was always ready at hand and easy to be seen by merely skillful attention. But the law has other tests of the invention than subtle conjecture of what might have been seen and yet was not (emphasis added).

The nasal dilator described herein, in view of the dramatic facts of the prior art as discussed above, indeed meets the strict requirements for true invention, and as supported by the foregoing Supreme Court decision as well as by many other court decisions over many years with similar holdings.

Having described my nasal dilator invention and explained why it has great novelty and utility, I claim:

1. A nasal dilator comprising in combination: spreading means having a portion for insertion in at least one nostril to move at least one wall thereof outwardly for increasing the opening of the nasal passage; and retaining means independent of the septum and operatively associated with said spreading means to maintain same in place for preventing said dilator from falling out of said nostril.

2. A nasal dilator comprising in combination: spreading means having a portion for insertion in the nasal opening to act on at least one nostril wall of the wearer for increasing the aperture of said nasal opening to improve the breathing of the wearer; and retaining means including a non-rigid member connected to said spreading means and also including attachment means adapted to be operatively connected to the wearer to hold said spreading means in place, for preventing said dilator from falling out of said nasal opening.

3. A nasal dilator comprising in combination: spreading means having a portion for insertion in the nasal opening to act on at least one nostril wall of the wearer for increasing said nasal opening to improve the breathing of the wearer; and retaining means including a flexible strip operatively connected to said spreading means and having adhesive means adapted to be pressed onto the outer nasal surface by the wearer, for preventing said dilator from falling out of said nasal opening.

4. A nasal dilator as defined in claim 3: and said flexible strip also including a small non-adhesive portion at the end of said strip to enable easy peeling of said adhesive means by the wearer for removal thereof from said outer nasal surface.

5. A nasal dilator comprising in combination: a UV-shaped spring having a central portion and two leg-portions for insertion in the nasal opening and acting on the two nostril walls for increasing said nasal opening to improve the breathing of the wearer; and retaining means including a flexible member connected to said UV-shaped spring at a central portion thereof and extending along both of said leg-portions and having adhesive means adapted to be pressed onto the outer nasal surface by the wearer to prevent said dilator from falling out of said nasal opening.

6. A nasal dilator comprising in combination; a UV-spring having a central portion and two leg-portions including contact portions at the ends thereof for insertion in the nasal opening formed by the nostril walls and acting on the inner surfaces thereof for increasing said nasal opening to improve the breathing of the wearer; retaining means comprising a flexible nasal strip connected to said UV-spring at the central portion thereof and extending along both of said leg-portions; and said strip including two end adhesive segments, adapted to be pressed onto the outer surfaces of said nostril walls by the wearer to prevent said UV-spring from falling out of said nasal opening.

7. A nasal dilator as defined in claim 5, and said flexible strip also including at least one non-adhesive segment between said two end-adhesive segments, for enabling the wearer to install said dilator without the fingers contacting said two adhesive segments and to determine the portion of the nose subjected to said end adhesive segments.

8. A nasal dilator as defined in claim 6; and resilient pad means operatively connected to each of said leg portions at said contact portions to provide the only contact of said leg portions with said inner surfaces of said nostril-walls to avoid discomfort for the wearer; and said flexible strip including at least one non-adhesive segment between said two end adhesive segments for enabling the wearer to install said UV-spring in said nasal openings without the wearer's fingers contacting said end adhesive segments, and to position a large share of said two end adhesive segments for adhering to said outer surfaces above the nose-flange.

9. A nasal dilator a defined in claim 6; and said flexible strip also including at least one thin semi-rigid but flexible non-adhesive piece attached to said nasal strip between said two end-adhesive segments for enabling the wearer to install said UV-spring in said nasal opening without the wearer's fingers contacting said adhesive segments, and to determine the portions of the outer nostril walls subjected to said end-adhesive segments.

10. A nasal dilator as defined in claim 6; and said retaining means including a single flexible non-adhesive segment between said two end-adhesive segments and extending about equal distances from said connection of said strip with said spring at said central portion thereof; and clamping means including a clamp-piece to secure said non-adhesive segment between said UV-spring and said clamp-piece at said central portion of said UV-spring, for enabling the wearer to install said leg-portions of said spring in said nasal opening without the wearer's fingers contacting said end-adhesive segments and to maintain alignment of said strip with said UV-spring.

11. A nasal dilator as defined in claim 6: and said UV-spring comprising substantially flat spring material; and said nasal strip including a single thin semi-rigid but flexible non-adhesive piece attached along its entire length to said nasal strip between said two end adhesive segments and extending about equal distances from said connection of said strip with said UV-spring at said central portion thereof; said non-adhesive piece having an aperture at the center thereof;

and clamping means including a clamp-piece retained by a screw and thread means for enabling said flexible non-adhesive piece to be inserted between said clamp-piece and said UV-spring with said screw positioned in said aperture to enable said screw and thread means to secure said flexible piece to said spring, for enabling the wearer to install said leg-portions of said spring in said nasal-openings without the wearer's fingers contacting said adhesive segments and to maintain alignment of said strip as a result of the transverse rigidity of said semi-rigid piece.

12. A nasal dilator as defined in claim 6; and pad means connected to said leg-portions of said UV-spring at said contact portions; said pad means including a resilient material having a substantially smooth surface with rounded edges for providing a degree of self-alignment in the only contact of said pad means with said inner surfaces of said nostril walls, to prevent said dilator from annoying the wearer.

13. A nasal dilator as defined in claim 6: and pad means connected to said leg-portions of said UV-spring at; said pad means including a soft resilient material having a substantially smooth outer surface for providing a degree of self-alignment in the only contact of said pad means with said inner surfaces of said nostril walls, to prevent said dilator from annoying the wearer; said pad means including a thin flexible cover enclosing said material to seal and protect same; and said pad means also including a thin skin-friendly flexible film having a portion connected on three sides to the back of said cover to form a pocket for enabling insertion of each of said leg-portions of said spring into one of said pockets between said cover and said film, for mounting and removing said pad means on said leg-portions of said UV-spring.

14. A nasal dilator as defined in claim 6: and pad means connected to said leg portions of said UV-spring at; said pad means including a soft resilient material having a substantially smooth surface with rounded edges for providing a degree of self-alignment in the only contact of said pad means with said inner surfaces of said nostril walls, to prevent said dilator from annoying the wearer; said pad means including a thin flexible cover enclosing said resilient material to seal and protect same; said pad means also including a thin flexible film having a portion extending beyond said cover and connected on three sides to the back of said cover to form a pocket for enabling insertion of each of said leg-portions of said UV-spring into one of said pockets between said cover and said film, for mounting and removing said pad means on said leg-portions of said UV-spring; and said extended portion including an adhesive segment on the side thereof adjacent to the spring-surface to secure said pad means to said leg portion.

15. A nasal dilator as defined in claim 6; and pad means connected to said leg-portions of said UV-spring at; said pad means including a resilient material having a substantially smooth surface for providing a degree of self-alignment in the only contact of said pad means with said inner surfaces of said nostril walls, to prevent said dilator from annoying the wearer; said pad means including a thin flexible cover enclosing said material to seal and protect same; said pad means also including a thin flexible film having a portion connected on three sides to the back of said cover to form a pocket for enabling insertion of each of said leg-portions of said spring into one of said pockets between said cover and said film, for mounting said pad means on said leg-portions; and said pad means having substantially parallel edges with tolerances disposed to produce a tight fit when each of said leg-portions of said spring is inserted into one pocket, for retaining said pad means on the end of each said leg-portion until removed by the wearer.

16. A nasal dilator as defined in claim 6; and pad means connected to said leg portions of said UV-spring at; hinge means operatively connecting said pad means to the end of each leg-portion of said UV-spring for providing self alignment of said pad means in the only contact thereof with said inner surfaces of said nostril walls, to prevent said dilator from annoying the wearer.

17. A nasal dilator as defined in claim 6; and pad means connected to said leg portions of said UV-spring at; hinge means operatively connecting said pad means to the end of each leg-portion of said UV-spring for providing self-alignment of said pad means in relation to the inner nasal walls; said hinge means including a base member; and said pad means including a relatively smooth outer surface and attached to said base member to provide the only contact of said UV-spring with said inner surfaces of said nostril walls, for preventing said dilator from annoying the wearer.

18. A nasal dilator as defined in claim 6; and pad means having a soft resilient material with a smooth surface and rounded edges connected to each of said leg portions at to provide the only contact of said UV-spring with said inner surface of said nostril-walls to avoid discomfort for the wearer; and said flexible strip including a semi-rigid but flexible non-adhesive piece attached to said nasal strip between said two end adhesive segments, for enabling the wearer to install said UV-spring in said nasal openings without the wearer's fingers contacting said adhesive segments and to position a large share of said end adhesive segments for adhering to said outer surfaces above the nose-flange.

19. A nasal dilator as defined in claim 6; and said leg-portions of said UV-spring having tab-portions at the ends thereof; pad means operatively connected to said tab-portions to provide the only contact of said UV-spring with said inner surface of said nostril-walls; and said tab-portions being bent somewhat inwardly to help in the proper alignment of said pad means with respect to the inner surfaces of said nostril-walls, to prevent said dilator from annoying the wearer.

20. A nasal dilator as defined in claim 5; and a non-adhesive segment comprising a single thin semi-rigid but flexible non-adhesive piece attached along its entire length to said flexible nasal strip between said two end adhesive segments and extending equal distances from said connection of said nasal strip with said UV-spring at the central portion thereof; and connecting means operatively associated with said non-adhesive piece to secure said non-adhesive piece to said central portion of said UV-spring, for enabling the wearer to install said contact leg-portions of said UV-spring in said nasal opening without the wearer's fingers contacting said end-adhesive segments and to maintain alignment of said strip with said spring as a result of the transverse rigidity of said semi-rigid piece.

21. A nasal dilator as defined in claim 6; and said flexible nasal strip also including small non-adhesive portions at the very ends thereof, to enable easy peeling of said adhesive segment by the wearer for removal thereof from said outer surfaces of said nostril walls.

22. A nasal dilator as defined in claim 6: and said two leg-portions including pad means operatively connected thereto at the contact portions thereof; said pad means including resilient material having a substantially smooth surface for providing a degree of self-alignment in the only contact of said pad means with said inner surfaces of said nostril walls, to prevent said dilator from annoying the wearer; and said pad means including a thin flexible skin-friendly cover enclosing said resilient material to seal and protect same for good hygiene.

23. A nasal dilator as defined in claim 6: and said UV-spring comprising substantially flat spring material, and said UV-spring and said flexible nasal strip including centering means for enabling the wearer to readily align the center of said nasal strip with the center of said UV-spring when installing each new nasal strip.

24. A nasal dilator as defined in claim 6: and pad means made of resilient material with a smooth surface and adapted to be connected to each of said leg portions at said contact portions thereof to provide the only contact of said leg-portions with said inner surfaces of said nostril walls; and said pad means including mounting means for attaching said pad means to said contact portions of each of said leg-portions and for removal therefrom, for enabling the wearer to replace said pad means whenever said resilient material takes an unacceptable permanent set.

25. A nasal dilator as defined in claim 6: and pad means made of resilient material with a smooth surface and adapted to be connected to each of said leg-portions at said contact portions thereof to provide the only contact of said leg-portions with said inner surfaces of said nostril walls; said pad means including mounting means for attaching said pad means to the extremity of each of said leg-portions and for removal therefrom, for enabling the wearer to replace said pad means whenever said resilient material takes an unacceptable permanent set; and said pad means including a thin cover made of skin-friendly flexible film to protect said pad means and promote good hygiene for the wearer.

26. A nasal dilator as defined in claim 6: and said UV-spring comprising substantially flat spring material; said nasal strip including an aperture at the center thereof; and said UV-spring including projecting means at the center thereof disposed to enter said aperture in said nasal strip, for enabling the wearer to readily align said center of said nasal strip with said center of said UV-spring when installing each new nasal strip.

27. A nasal dilator as defined in claim 6: and pad means connected to said leg-portions of said UV-spring at said contact portions thereof; said pad means including a soft resilient material having a substantially smooth outer surface for providing a degree of self-alignment in the only contact of said pad means with said inner surfaces of said nostril walls, to prevent said dilator from annoying the wearer; said pad means including a thin skin-friendly flexible cover enclosing said meterial to seal and protect same; and said flexible nasal strip also including small non-adhesive portions at the very ends thereof adjacent to said end-adhesive segment, to enable easy peeling of said end-adhesive segments by the wearer for removal thereof from said outer surfaces of said outer nostril walls.

28. A nasal dilator as defined in claim 6: and pad means connected to said leg-portions of said UV-spring at said contact portions thereof; said pad means including a soft resilient material having a substantially smooth outer surface for providing a degree of self-alignment in the only contact of said pad means with said inner surfaces of said nostril walls, to prevent said dilator from annoying the wearer; and said flexible nasal strip also including small non-adhesive portions at the very ends thereof adjacent to said end-adhesive segments, to enable easy peeling of said end-adhesive segments by the wearer for removal thereof from said outer surfaces of said nostril walls; said UV-spring comprising substantially flat spring meterial; said nasal strip including an aperture at the center thereof; and said UV-spring including projecting means at the center thereof disposed to enter said aperture in said nasal strip, for enabling the wearer to readily align said center of said nasal strip with said center of said UV-spring when installing each new nasal strip.

29. A nasal dilator comprising in combination, a UV-spring having a central portion and two leg-portions including contact portions at the ends thereof for insertion in the nasal opening formed by the nostril walls without contacting the septum and acting on the inner surfaces of said nasal walls for increasing said nasal opening to improve the breathing of the wearer; and retaining means comprising a flexible nasal strip connected to said UV-spring at the central portion thereof and extending along both of said leg-portions; said strip including two ends adhesive segments adapted to be pressed onto the outer surfaces of said nostril walls by the wearer to prevent said spring from falling out of said nasal opening; said flexible nasal strip including a third adhesive segment at the center thereof between said two end-adhesive segments and adapted to be pressed by the wearer onto said central portion of said UV-spring for attaching said flexible nasal strip thereto; said third adhesive segment having a length disposed to provide two non-adhesive segments between said two end adhesive segments and said third adhesive segment, for enabling the wearer to install said dilator without the wearer's fingers contacting said end adhesive segments and to determine the area of said two outer nostril walls subjected to said end adhesive segments.

30. A nasal dilator defined in claim 29: and said UV-spring comprising substantially flat spring material prebent into a UV-shape in its free position; and centering means comprising, an aperture at the center of said nasal strip, and projecting means at the center of said UV-spring disposed to enter said aperture, for enabling the wearer to readily align said center of said nasal strip with said center of said UV-spring when installing each new nasal strip.

31. A nasal dilator comprising in combination: spreading means adapted to be inserted in the nasal opening formed by the nostril-walls of the wearer to move said walls outwardly for increasing said nasal opening to improve the breathing of the wearer; said spreading means comprising a UV-spring having a central portion and two leg-portions including contact portions at the ends thereof for insertion into said nasal opening without contacting the septum to apply a predetermined force on the inner surfaces of said nostril-walls for producing said outward movement thereof; said UV-spring comprising flat bendable spring material for enabling the wearer to select any amount of said predetermined force by slight bending of said UV-spring in small steps to provide a desired amount of said nasal opening; retaining means comprising a flexible nasal strip operatively connected to said UV-spring at the central portion thereof and including two end-adhesive segments disposed to be pressed by the wearer onto the outer surfaces of said two nostril-walls with a smooth surface to maintain said dilator in place; said leg-portions of said UV-spring at said contact portions including pad means to provide the only contact of said spring with said inner surfaces of said nostril-walls, to avoid discomfort for the wearer; and said flexible nasal strip also including at least one non-adhesive segment between said two end-adhesive segments for enabling the wearer to install said spring in said nasal openings without the wearer's contacting said adhesive segments, and to position a large share of said adhesive segments to adhere to said outer surfaces above the nose-flange.

32. A nasal dilator as defined in claim 31; wherein said pad means having a resilient material and a thin flexible cover enclosing said resilient material to seal and protect same; said pad means also including a thin flexible film having a portion connected on three sides to the back of said cover to form a pocket for enabling insertion of each of said leg-portions of said spring into one of said pockets between said cover and said film, for mounting said pad means on said leg-portions of said UV-spring.

33. A nasal dilator as defined in claim 31; and said non-adhesive segment comprising at least one thin semi-rigid piece attached to said nasal strip between said two end-adhesive segments, to determine the portion of the outer nostril walls subjected to said end-adhesive segments.

34. A nasal dilator as defined in claim 31; and said flexible nasal strip including a third adhesive segment at the center thereof to be pressed by the wearer onto said central portion of said UV-spring to connect said flexible nasal strip thereto; said third adhesive segment having a length disposed to provide two non-adhesive segments between said two end adhesive segments and said third adhesive segment, for enabling the wearer to install said dilator without the wearer's fingers contacting said adhesive segments and to determine the portion of the outer nasal walls subjected to said end adhesive segments.

35. A nasal dilator as defined in claim 31; and hinge means operatively connecting said pad means to the said extremity of each leg-portion of said UV-spring for providing a free self-alignment of said pad means in relation to said inner nostril walls; said hinge means including a base member; and said pad means also including a material with a relatively smooth surface and rounded edges attached to said base member to provide said only contact of said pad means with said inner surfaces of said nostril-walls, for preventing said dilator from annoying the wearer.

36. A nasal dilator as defined in claim 31: and said flexible nasal strip also including small non-adhesive portions at the very ends of said strip, to enable easy peeling of said adhesive segments near the two ends of said strip by the wearer for removal thereof from said outer surfaces of said two nostril walls.

37. A nasal dilator as defined in claim 31: and said pad means including soft resilient material having a substantially smooth outer surface with rounded edges for providing a degree of self-alignment in the only contact of said pad means with the inner surfaces of said nostril walls, to prevent said dilator from annoying the wearer; and said pad means including a thin flexible skin-friendly cover enclosing said resilient material to seal and protect same for good hygiene.

38. A nasal dilator as defined in claim 31: and said non-adhesive segment comprising a single thin semi-rigid but flexible non-adhesive piece attached along its entire length to said flexible strip between said two end adhesive segments and extending equal distances from said connection of said strip with said UV-spring at the central portion thereof; and connecting means operatively associated with said non-adhesive piece for securing said non-adhesive piece to said central portion of said spring, for enabling the wearer to install said leg-portions of said UV-spring in said nasal opening without the wearer's fingers contacting said adhesive segments and to maintain alignment of said strip with said spring as a result of the transverse rigidity of said semi-rigid piece.

* * * * *

UNITED STATES PATENT AND TRADEMARK OFFICE
CERTIFICATE OF CORRECTION

PATENT NO. : 6,238,411 B1
DATED : May 29, 2001
INVENTOR(S) : Robert H. Thorner

It is certified that error appears in the above-identified patent and that said Letters Patent is hereby corrected as shown below:

Column 4,
Line 5, after "which" insert -- can --.
Line 36, after "wearer" insert -- for attachment thereto --.

Column 5,
Line 6, after "(selectable" should read -- (selectable) --.

Column 8,
Line 30, "FIGS. 4 and 5 show the" should start a new paragraph.

Column 10,
Between lines 33 and 34, insert the following:
--     For example, the nasal strip 4 of Fig. 3 is unchanged if the two non-adhesive segments 8 comprise a single continuous piece (like thin flexible plastic) and in the same position as shown for the two plastic pieces 8; the adhesive segment 6 will then comprise a separate adhesive material applied to the single plastic piece 8 on the same side and located in the same central position as for the exposed adhesive segment 6. In this form of nasal strip, the structure and operation are unchanged since the now single non-adhesive segment 8 and adhesive segment 6 appear exactly the same as illustrated in Fig. 3, and are used in exactly the same manner as discussed above; then the single plastic piece 8 is exactly the same as the single plastic piece 18 in Fig. 8, except for the centering apertures, wherein the slot 19 in Fig. 8 is replaced with the hole 6a in Fig. 3.
    For another example, the plastic pieces 8 in Fig. 3 might be omitted and replaced with two non-adhesive sections in a single adhesive strip 4, with only the other two non-adhesive segments 8a at the ends of strip 4. But the form of nasal strip shown in Fig. 3 enables easier installation for the wearer.
    In still another variation, the plastic film 13 of the covered pad in Fig. 6 may be omitted, and replaced with a strong adhesive, so the pad assembly can be attached by adhesive to contact-portion 3 and removed by the wearer. But the form of Fig. 6 is easier to install and more hygienic.

UNITED STATES PATENT AND TRADEMARK OFFICE
CERTIFICATE OF CORRECTION

PATENT NO. : 6,238,411 B1
DATED : May 29, 2001
INVENTOR(S) : Robert H. Thorner

It is certified that error appears in the above-identified patent and that said Letters Patent is hereby corrected as shown below:

The patent system is actually a "social contract" between the general public and any citizen who chooses to take the high risks and cost of developing and promoting an invention. The public in effect is saying to the inventors: "If you will take these high risks to give us something new which is much better than anything in the past, we will give you for 20 years from your filing date the exclusive right to exploit your invention by preventing the manufacture, use and sale by others."
However, this right is granted only providing the inventor comes forth with a new thing that is workable and not just an improvement in design that would be obvious to those skilled in the art; it must provide a dramatic improvement and give this dramatic result in actual practice of the invention when the public can buy it on the open market. In other words, a valid patent cannot be obtained for something that is just different -- it must pass the strict tests established by the Patent Office and court decisions. --.

Column 11,
Line 63, "similarly" should read -- Similarly --.

Column 13,
Line 15, "the patent law abounds in illustrations" should read -- *the patent law abounds in illustrations* --.
Lines 20 and 21, "Knowledge after the event is always easy" should read -- *Knowledge after the event is always easy* --, and "seemed to have eluded the search of the world" should read -- *seemed to have eluded the search of the world* --.
Line 51, delete "wearer" and insert -- the outer surface of the nose --.

Column 14,
Line 23, "5" should be -- 6 --.
Line 27, after "two" insert -- end- --.

UNITED STATES PATENT AND TRADEMARK OFFICE
CERTIFICATE OF CORRECTION

PATENT NO. : 6,238,411 B1
DATED : May 29, 2001
INVENTOR(S) : Robert H. Thorner

It is certified that error appears in the above-identified patent and that said Letters Patent is hereby corrected as shown below:

Column 15,
Line 20, after "at" insert -- said contact portions --.
Line 35, after "at" insert -- said contact portions --.
Line 53, after "at" insert -- said contact portions --.

Column 16,
Line 4, after "at" insert -- said contact portions --.
Line 11, after "at" insert -- said contact portions --.
Line 22, after "at" insert -- said contact portions --.
Line 42, "5" should be -- 6 --.
Line 59, "segment" should be -- segments --.

Column 17,
Line 26, "the extremity" insert -- said contact portion --.

Column 18,
Line 55, after "nostril-walls" delete -- with a smooth surface --.
Line 57, after "means" insert -- with a smooth surface --.
Line 64, before "adhesive" insert -- end- --.
Line 66, "wherein" should read -- and --.

Signed and Sealed this

Fifth Day of February, 2002

Attest:

JAMES E. ROGAN
*Director of the United States Patent and Trademark Office*

*Attesting Officer*